United States Patent
Draenert

(10) Patent No.: US 6,770,100 B2
(45) Date of Patent: Aug. 3, 2004

(54) MODULAR REVISION PROSTHESIS

(76) Inventor: Klaus Draenert, Gabriel Max Strasse 3, D-81545 Munich (DE)

( * ) Notice: Subject to any disclaimer, the term of this patent is extended or adjusted under 35 U.S.C. 154(b) by 0 days.

(21) Appl. No.: 09/919,179

(22) Filed: Jul. 30, 2001

(65) Prior Publication Data

US 2002/0045950 A1 Apr. 18, 2002

(30) Foreign Application Priority Data

Jul. 29, 2000 (DE) .......................... 100 36 984

(51) Int. Cl.[7] ................................. A61F 2/36
(52) U.S. Cl. .................................. 623/23.26
(58) Field of Search .................. 623/23.26, 23.18, 623/23.27, 23.15, 23.19, 23.24, 23.33, 23.35

(56) References Cited

U.S. PATENT DOCUMENTS

| | | | | |
|---|---|---|---|---|
| 3,846,846 A | * | 11/1974 | Fischer ......................... | 411/33 |
| 4,878,917 A | * | 11/1989 | Kranz et al. .............. | 623/23.45 |
| 4,878,919 A | * | 11/1989 | Pavlansky et al. ....... | 623/23.18 |
| 4,895,572 A | * | 1/1990 | Chernoff ..................... | 606/64 |
| 5,489,309 A | * | 2/1996 | Lackey et al. ........... | 623/19.14 |
| 5,507,830 A | * | 4/1996 | DeMane et al. ......... | 623/22.42 |
| 5,702,480 A | * | 12/1997 | Kropf et al. .............. | 623/23.15 |
| 5,702,486 A | * | 12/1997 | Craig et al. .............. | 623/19.14 |
| 6,030,417 A | * | 2/2000 | Bresler et al. ........... | 623/23.15 |
| 6,102,956 A | * | 8/2000 | Kranz ....................... | 623/23.15 |
| 6,136,035 A | * | 10/2000 | Lob et al. ................ | 623/20.15 |
| 6,238,436 B1 | * | 5/2001 | Lob et al. ................ | 623/22.42 |
| 6,264,699 B1 | * | 7/2001 | Noiles et al. ............ | 623/23.23 |
| 6,432,110 B1 | * | 8/2002 | Richelsoph ................. | 606/62 |
| 2001/0008981 A1 | * | 7/2001 | Masini ..................... | 623/22.42 |
| 2002/0007220 A1 | * | 1/2002 | Gie et al. ................ | 623/23.15 |
| 2002/0040244 A1 | * | 4/2002 | Despres et al. .......... | 623/22.15 |

* cited by examiner

Primary Examiner—Eduardo C. Robert
(74) Attorney, Agent, or Firm—Westman, Champlin & Kelly, P.A.

(57) ABSTRACT

A modular prosthesis for replacement of hip joints has a shaft that fits into the femur canal to replace a previous prosthesis, which is made up of sections aligned and held on a cylinder that extends through the sections. In this matter, the length of the shaft can be changed to insure that the shaft will be aligned with bone sections that have not been damaged from the previous prosthesis. The shaft includes a shoulder segment adjacent the proximal end of the femur to attach to ball or head prosthesis using tension carrying screws or elements.

5 Claims, 2 Drawing Sheets

MODULAR REVISION PROSTHESIS

BACKGROUND OF THE INVENTION

In order to restore the function of a loose artificial hip joint, various major and minor problems have to be surmounted. The major problems are the anchorage problems related to achieving stable fixation despite often large defects remaining in the bony support after the joint components have been removed. Minor problems involve filling in the defects with bone from tissue banks; this is accomplished using "morcellized bone" plastics of the appropriate size. (Lamerigts, N. M. P., 1998. Proefschrift an der katholischen Universitt Niymegen.) Once the bony support structure has been reinforced with bone from tissue banks, the corresponding joint replacement components can be cemented in.

In order to use such a procedure, the bony structures must be sufficiently stable to achieve a stable overall anchorage. However, these bone structures often are no longer present, and as a result, very special demands are placed on the implant. Therefore, there is a genuine need for systems that can be adapted to the given situation that is when large defects are present, and that take various biomechanical fixation principles into account. With this background as a foundation, a novel approach to the problem of revision operations (i.e., replacement of the femur component of a prosthesis) was unexpectedly discovered.

PRIOR ART

The extent of the defects in the bony femur bed after the removal of a loose, previously implanted prosthesis may vary. This has led to attempts to classify bone defects, for example in the DGOT (Bettin, D., Katthagen, B. D., (1997), Die DGOT-Klassifkation von Knochendefekten bei Huft-Totalendoprothese-Rev-isionsoperationen [The DGOT Classification of Bone Defects in Total Hip Endoprosthesis Revision Operations], Z. Orthop. 135). In some cases, the bone damage is considerable. Treatment of the loose prosthesis or implant components involves complete removal of the components and, if present, the bone cement that was previously used, as well as all of the connective tissue surrounding the previous implant, that connects the implant to the bone. Not until this has been done can one realistically assess the extent of bone loss. Often, the only way to anchor a new implant component is to reach beyond all defects and anchor the component deep in the portion of the femur diaphysis (the shaft of the long bone) that is still healthy, frequently without the use of cement.

Another method is to reconstruct the bone with morcellized bone from tissue banks and use cement to reattach such a component. This is described in detail in Lamerigts, N. M., (1998), The Incorporative Process of Morcellized Bone Graft. Proefschrift University Nijmegen (Catholic University). In both cases, proximal anchoring, that is, near the upper end of the bone is usually not stable. The implants in the femur are usually very long and heavy, and much poorer results are obtained than in primary operations.

Tests and simple experiments on cadaver bones unexpectedly revealed very efficient ways to anchor and fix femur components in defective bone support structures, even components having short shafts.

SUMMARY OF THE INVENTION

A prosthesis anchorage system comprises a modular replacement insert for the femur for repairing artificial hip joints. The anchorage system provides a femur stem that is segmented and will insert into the femur canal, and can be elongated to a length so that portions of the femur stem will be aligned in the canal with bone that provides a solid holding action for the stem when replacing a previously installed stem that has become loosened. The base modular section includes an axial or central cylinder that inserts into adjacent stem sections and which serves to hold the stem sections in alignment. At the proximal end of the femur, a shoulder stem section is used. The shoulder stem section has a surface that will permit attaching a mating shoulder on a neck and head prosthesis securely with tension carrying members.

The length of the femur stem inserted into the femur canal can be adjusted to accommodate a wide variety of conditions when a hip joint is to be replaced.

DESCRIPTION OF THE INVENTION

Figure 1:
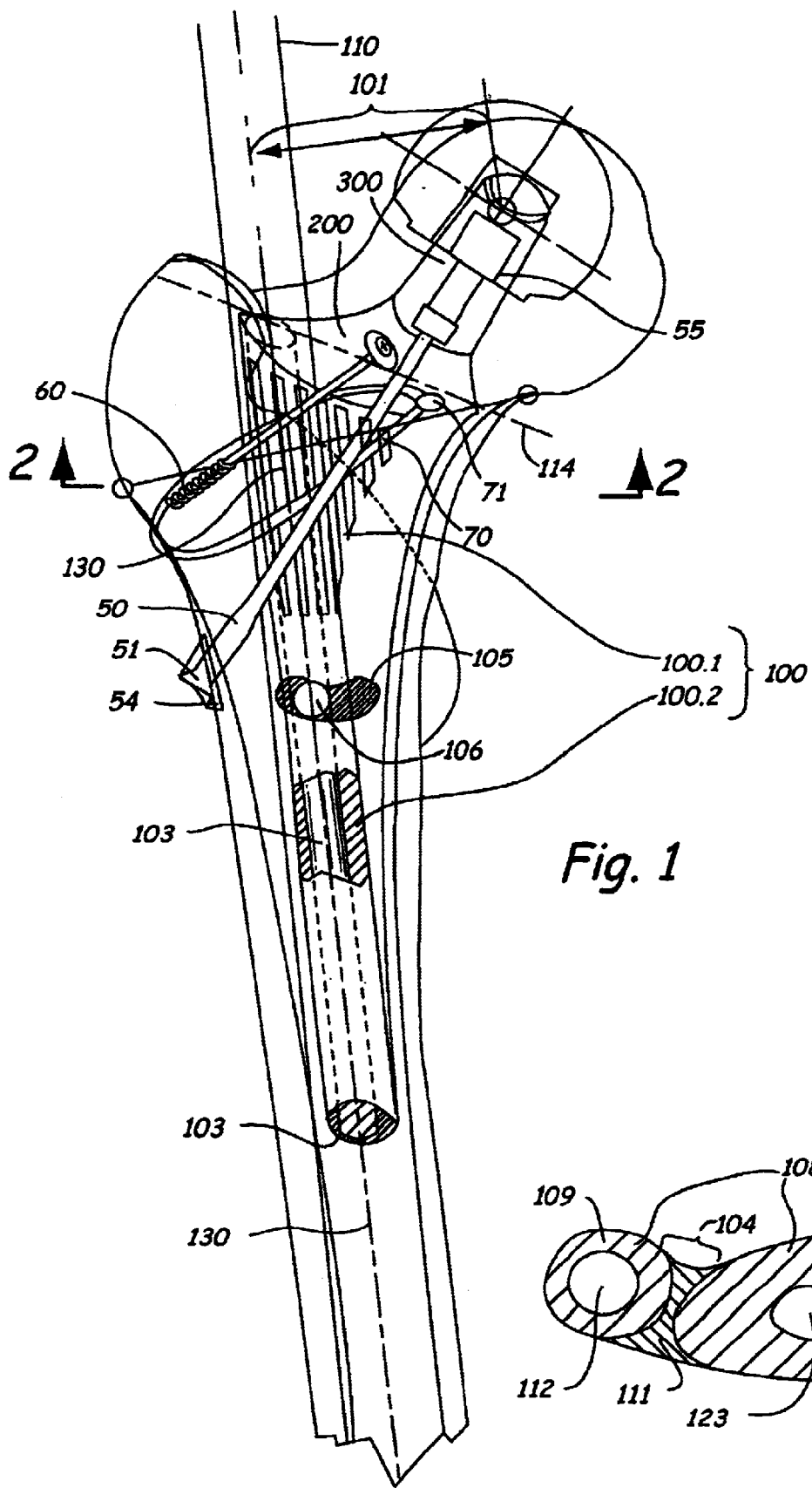
FIG. 1 is a view of femur shaft for a prosthesis illustrated schematically in place.

The modular tension anchorage system of the present invention allows one to adapt the implant to various defect conditions encountered in revising (replacing) a loose femur implant stem or shaft component. The invention takes various defects that have t be dealt with into account with regard to the stem or shaft length and various additional anchoring possibilities in the proximal femur canal. The modular system essentially is comprised of a femural or medullary stem or shaft (100), made up of one or more stem segments. The femural stem or shaft 100 corresponds in size to a cylinder opening in the bone forming the femural or medullary canal, the projection lines of which are indicated at 110A in FIG. 1, and which canal is located around the medullary canal axis 130.

Various stem segments must be used in sequence along this open cylinder along the medullary or femural canal and centered on the canal axis 130. The base or distal stem segment (100.3) may be of various lengths, and it is always comprised of the tip (102) and an axial or center cylinder (103). One stem segment—in rare instances two or more stem segments (100.2, 100.3)—may be arranged on top of each other along the axial cylinder (103). A shoulder segment (100.1) always follows or is placed above the inserted stem. The contact surface (105) on the proximal or upper end the base stem segment 100.3 is concave. The corresponding or mating distal end of the center or next higher stem segment is convex, or vice versa. The corresponding or mating ends of the stem segments may also engage one another conically or in other words with the end of one segment having a cone shape and the end of the adjacent segment having a mating receptacle. A curved, interlocking surface design between the ends of the adjacent segments has proved to be particularly effective. Such a surface prevents rotation and takes tension loads on the lateral side of the stem and compression loads on the medial side of the stem into account.

Figure 2:
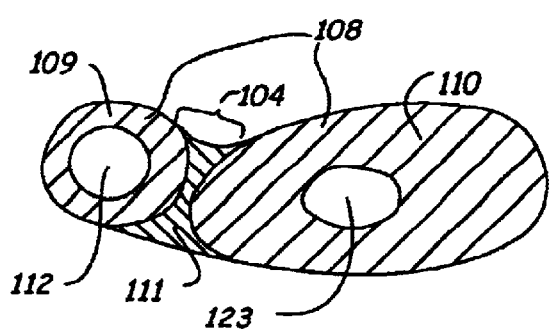
FIG. 2 is a fragmentary sectional view taken as on line 2—2 in FIG. 1.

The axial cylinder (103) and the corresponding hole centered on axis 130 in which the axial cylinder 103 fits in the adjacent stem segments or shoulder segment 100.1 are smooth, or they are structured with a locating groove and nubs to prevent rotation. The length of the prosthesis is determined based on how far it needs to extend into the femur canal so the distal end is beyond bone defects. A center stem segment (100.2) is inserted with the hole (106) receiving the central axial cylinder (103) that is also in the base segment (100.3). The cross section (108) of the metaphysial or proximal shoulder segment (100.1) as shown in FIG. 2 consists of the lateral cylinder (112), which is hollow (109), for receiving the central axial cylinder (103). The connecting segment (111), joins the lateral cylinder (112) and the medial portion (110), and the connecting segment (111) forms the convex-concave (104) convex contour of the dorsal side. The channel for the tension anchor (thrust rod) (50) passes through bore (113) across the extended areas of the medial portion of the metaphysial shoulder segment (100.1).

Figure 3:
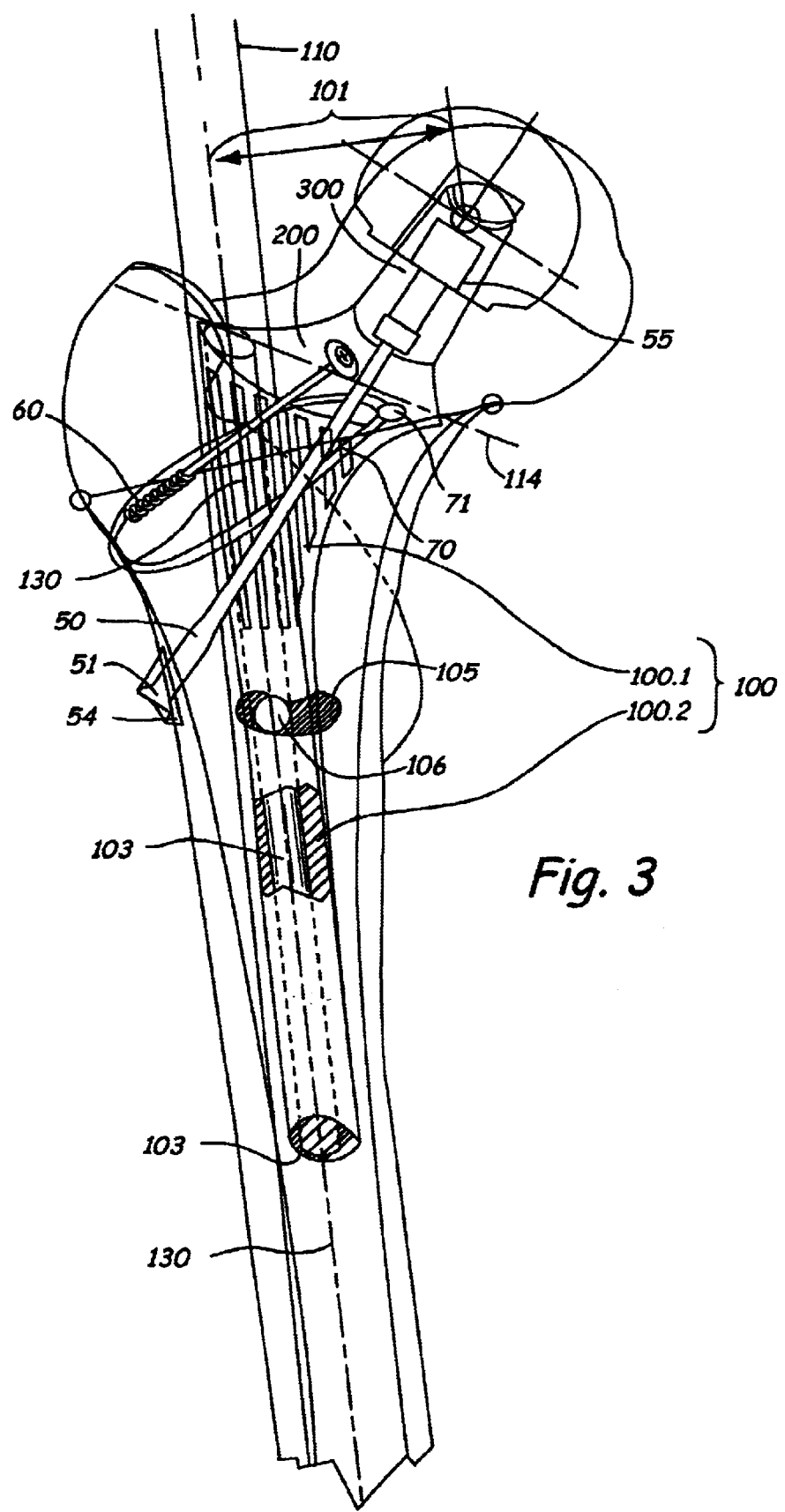
FIG. 3 is a view similar to FIG. 1 with a modified construction.

The metaphysial shoulder segment (100.1) exhibits a parabolically curved concave outer surface (See FIGS. 1 and 3) medially, ventrally, and dorsally in a U-shape for force transfer. The outer surface of the shoulder segment is centered on a collum centrum axis that is the central axis of the head prosthesis 301 and the central axis of the cone 300. The head prosthesis includes a neck having a base 200 and a ball at an outer end. The base (200) of the the head prosthesis (301) has additional holes for tension anchors (60) and cables ((70) in a bore (71)). The thrust anchor (50) is held in the cone (300) of the prosthesis (301), and axially through the cone (300) like a tension screw, as shown, having a washer (54) and screw head (51) so the anchor (50) can be threaded into a nut (55) in the cone (300). The nut (55) in the cone (300) is prevented from turning. The other tension anchors can also be embodied as simple tension screws (for example 60), in which case the screw head would be located in the shoulder (200) and the tension screw would extend through the shoulder so the thread would be located on and threaded into the lateral side of the femur bone to anchor the tension screw or tension carrying member in the femur.

EXAMPLE

After making absolutely sure the diagnosis is loosening of the implanted hip prosthesis, the joint is exposed via the old access incision. The scar tissue is carefully removed, the joint is dislocated or separated from the femur shaft generally along plane 114, and the old, loose femur shaft is removed. Usually the old shaft can simply be pulled out; in a rare case, an instrument needs to be used to hammer it out. The old bone cement and connective tissue in the femur canal are then carefully removed. An ultrasonic titanium chisel can be very useful in this procedure.

The bone channel, or femur canal from which the connective tissue has been removed, is rinsed carefully using a jet lavage, and the bony structure is then reconstructed. To do this, tissue bank bone is ground up in a mill, and this "morcellized" bone is mixed in a 50:50 ratio with a shell-shaped bone ceramic used as the granulate—for example: Synthacer.RTM.—and it is then forced up against the walls in the intermedullary or femur canal with the aid of a trial shaft. Drainage tubes are then inserted into the canal via the fossa intertrochanterica, and a vacuum is applied to these drainage tubes.

Then, the intermedullary tissue is carefully rinsed with $H_2O_2$ and the canal is filled with bone cement using a snorkel application system. The prosthesis stem assembly of the necessary length stem segments including at least the base stem segment (100.3) and, if needed, one other stem segment, and also the shoulder segment (100.1) are axially inserted into the femur bone canal, which is filled with bone cement and morcellized bone. After the cement has cured with the new femur stem and shoulder segment in place, a hole (113) is drilled in the prosthesis shoulder segment along the axis of the cone (300), and, if necessary, additional holes are drilled through the shoulder segment and cone, and the cone (300) is stably anchored into the bone of the femur by means of tension anchors (50) or tension screws (60) that extend through the femur and shoulder segment to clamp the cone in place. The cone is positioned so the offset 101 of the center of rotation to the axis 130 is correct. The screws (60) can also be advantageously screwed in through the still-soft cement, provided that holes were drilled in advance in the femur. The advantage of this is that the bone cement shrinks onto the screw thread.

If conditions in the femur bone are still stable after removal of the old implant, the prosthesis stem system can also be anchored stably in the femur bone without using bone cement.

What is claimed is:

1. A femoral component for an artificial hip joint, said femural component comprising:

a base stem segment comprising a tip portion and a cylinder portion extending outwardly from the tip portion along a diphysial axis, and additional segments including at least a shoulder segment for a proximal end of a femur and each additional segment having a bore to be centered on the diaphysial axis, the bore of each additional segment receiving the cylinder extending throughout the entire additional segment along the diaphysial axis and the bore of each additional segment receiving the outwardly extending cylinder portion extending along the diaphysial axis, the cylinder portion in the bore of each additional segment forming the sole member to hold the segments, including at least the base segment and the shoulder segment with the bores in axial alignment.

2. The femural component of claim 1 further including an intermediate stem segment fitted on the cylinder portion between the base stem segment and the shoulder segment.

3. The femural component of claim 1 wherein the shoulder segment has a surface formed around a collum centrum axis for mounting a base of a support for a head prosthesis lying along and centered on the collum-centrum axis.

4. The femural component of claim 1 wherein the stem segments support a head prosthesis having a central axis and a support surface, the shoulder segment having a medial surface centered around the central axis of the head prosthesis and at least one tension carrying member anchored in the head prosthesis and clamping the support surface of the head prosthesis against the medial surface of the shoulder segment, said tension carrying member extending to the exterior of a femur to hold the medial surface and support surface together when the segments and head prosthesis are supported on a femur.

5. The femural component of claim 4 wherein the medial surface on the shoulder segment is concave and the support surface on the head prosthesis is complimentary in shape.

* * * * *